United States Patent
Eroma et al.

(10) Patent No.: US 7,838,055 B2
(45) Date of Patent: Nov. 23, 2010

(54) CRYSTALLIZATION OF POLYOL COMPOSITIONS, CRYSTALLINE POLYOL COMPOSITION PRODUCT AND USE THEREOF

(75) Inventors: Olli-Pekka Eroma, Kotka (FI); Johanna Nygren, Lohja (FI); Heikki Heikkila, Espoo (FI); Per Bo Sorensen, Copenhagen (DK); Marja-Leena Sarkki, Kantvik (FI); Ian Fairs, Uckfield (GB); Hakan Gros, Kantvik (FI)

(73) Assignee: Danisco Sweeteners Oy, Espoo (FI)

( * ) Notice: Subject to any disclaimer, the term of this patent is extended or adjusted under 35 U.S.C. 154(b) by 732 days.

(21) Appl. No.: 10/517,692

(22) PCT Filed: Jul. 2, 2003

(86) PCT No.: PCT/FI03/00533
§ 371 (c)(1),
(2), (4) Date: Jul. 5, 2005

(87) PCT Pub. No.: WO2004/005227
PCT Pub. Date: Jan. 15, 2004

(65) Prior Publication Data
US 2006/0025584 A1 Feb. 2, 2006

(30) Foreign Application Priority Data
Jul. 3, 2002 (FI) ................................. 20021312

(51) Int. Cl.
*A23C 3/037* (2006.01)
*A23L 1/236* (2006.01)
*A23G 4/00* (2006.01)
*C07H 1/06* (2006.01)
*C07H 1/08* (2006.01)

(52) U.S. Cl. .................. 426/471; 426/474; 426/473; 426/548; 426/3; 426/467; 536/127

(58) Field of Classification Search ............... 426/471, 426/473, 474, 548, 3, 467; 536/127
See application file for complete search history.

(56) References Cited

U.S. PATENT DOCUMENTS

| 5,017,400 | A | * | 5/1991 | Olinger et al. ............... 426/660 |
| 5,580,601 | A | | 12/1996 | Ribadeau-Dumas et al. |
| 5,637,334 | A | | 6/1997 | Yatka et al. |
| 5,900,261 | A | | 5/1999 | Ribadeau-Dumas et al. |
| 5,958,471 | A | | 9/1999 | Schwarz et al. |
| 6,165,511 | A | | 12/2000 | Schwarz et al. |
| 6,395,893 | B1 | * | 5/2002 | Heikkila et al. ............. 536/120 |
| 6,764,706 | B1 | * | 7/2004 | Heikkila et al. ............. 426/548 |
| 6,821,535 | B2 | * | 11/2004 | Nurmi et al. ................... 426/5 |

FOREIGN PATENT DOCUMENTS

| DE | 196 15 418 A1 | 10/1997 |
| WO | WO A1 91 07 100 | 5/1991 |
| WO | WO 99/47532 | * 9/1999 |
| WO | WO 9959426 | 11/1999 |

OTHER PUBLICATIONS

EP Office Action for Applicaion No. 03 735 749.8 dated Mar. 26, 2010.

* cited by examiner

*Primary Examiner*—Shaojia Anna Jiang
*Assistant Examiner*—Scarlett Goon
(74) *Attorney, Agent, or Firm*—Scully, Scott, Murphy & Presser, P.C.

(57) ABSTRACT

The present invention relates to a microcrystallized polyol comprising at least two polyols, wherein said polyols are selected from the group consisting of maltitol, xylitol and lactitol and wherein said composition contains at least 25% by weight of each of at least two of said polyols microcrystallized together into a solid microcrystalline product. The present invention also relates to a process for the microcrystallization of polyols into a polyol composition. The microcrystallized polyol composition can be used in confectionery, foodstuffs, oral hygiene products and pharmaceuticals and in dietetic products.

16 Claims, 2 Drawing Sheets

Figure 1:
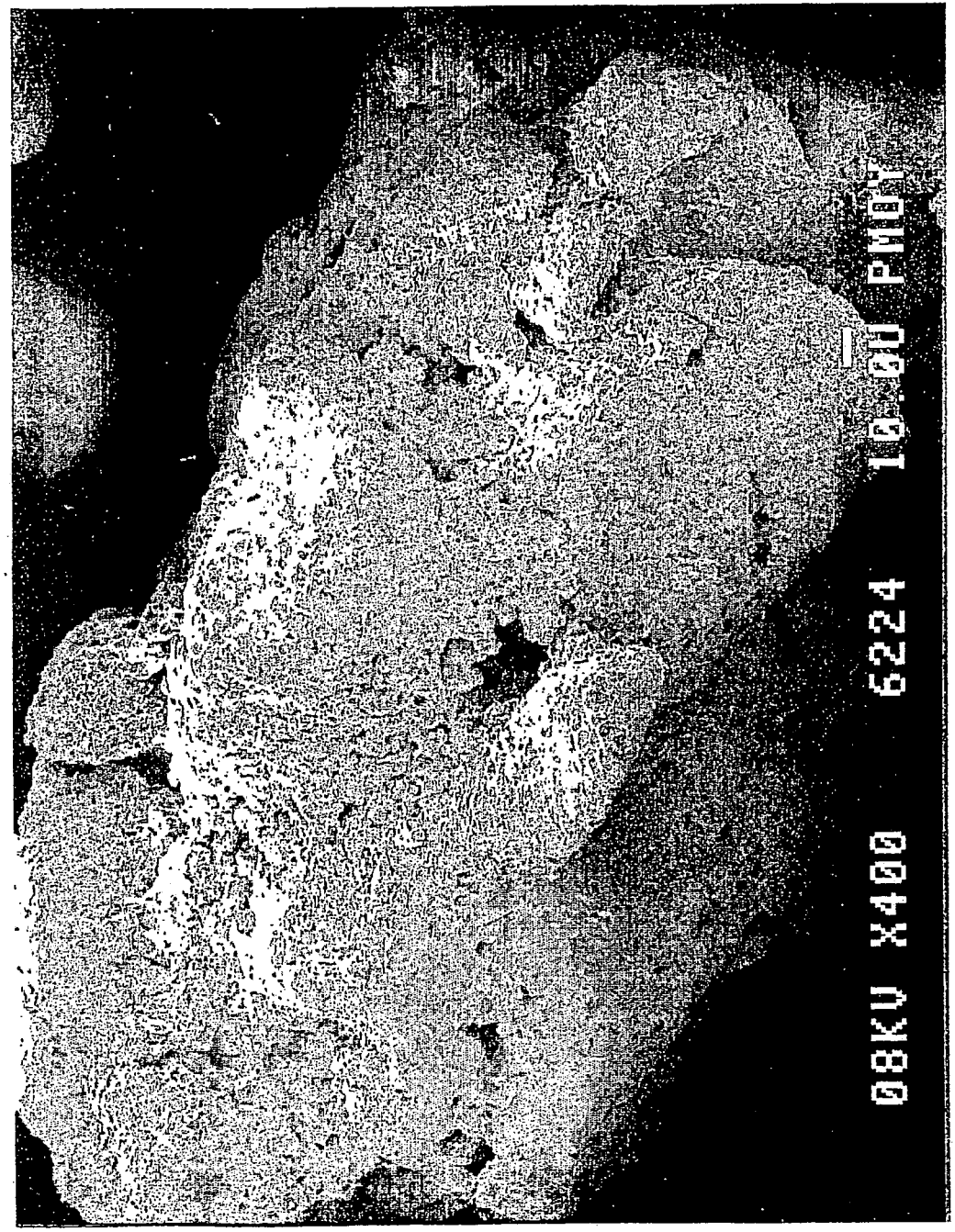

CRYSTALLIZATION OF POLYOL COMPOSITIONS, CRYSTALLINE POLYOL COMPOSITION PRODUCT AND USE THEREOF

FIELD OF THE INVENTION

The present invention relates to a microcrystallized polyol composition having novel properties, to a process for the microcrystallization of the polyol composition and to the use thereof in confectionery, foodstuffs, oral hygiene products and pharmaceuticals and in dietetic products. The polyol composition of the present invention is based on a mixture of at least two polyols selected from maltitol, xylitol and lactitol. The present invention specifically provides a microcrystalline polyol composition wherein the crystals are produced by microcrystallization of the polyol composition from a liquid polyol solution.

BACKGROUND OF THE INVENTION

Polyols are attractive as sugar substitutes in food contexts because of their metabolic, dental and technical characteristics. Among the polyols maltitol, xylitol and lactitol have gained wide acceptance in various applications in the food and pharmaceutical industry.

Maltitol is a polyol which is commercially produced by the hydrogenation of maltose. Maltitol has a sweetness, which is about 85 to 95% that of sucrose and it exhibits a weak cooling effect when dissolving in the mouth. Maltitol is non-cariogenic and non-insulin-dependent which promotes its use as a sugar substitute in confectionery and dietetic foods.

Maltitol has a melting point of 148-151° C. and a solubility of 62% (w/w) in water at 20° C. and it was for a long time available only as a syrup since it was difficult to crystallize and since spray drying of maltitol produces a sticky hygroscopic powder which adheres to the walls of the equipment. The prior art indicates that no method for the crystallization of maltitol from impure solutions is known and that even the crystallization of pure maltitol is slow and complicated.

Thus, EP 0 491 953 describes a method for the crystallization of maltitol by feeding a maltitol solution to an extruder, adding maltitol seed crystals, cooling and kneading and then extruding the resulting magma through a nozzle. According to the patent, spray drying of maltitol is problematic since maltitol tends to form supersaturated solutions and has a low rate of crystallization. Spray drying resulted in sticky and glassy products which were not satisfactory.

In US JP 9110891 the problems with spray drying of maltitol were solved by first causing precrystallization of maltitol in an aqueous maltitol solution having a maltitol purity of 85-99.9% by weight during 5 to 30 hours to provide a massecuite of maltitol containing up to 50% suspended crystals and then spraying the massecuite into drying air. The resulting product was aged for 10 hours and then additionally dried.

In U.S. Pat. No. 4,408,041 and its divisional patent U.S. Pat. No. 4,717,765 seed crystals of maltitol having a purity of 99.8% were added to an 80% maltitol solution to provide a mascuite which was then spray dried, fluidized and aged to provide a crystalline product.

In U.S. Pat. No. 5,873,943 a maltitol syrup having a purity of 92 to 99.9% was condensed, crystallized to provide seed crystals and spray dried to provide a solid containing crystalline maltitol.

Finally, U.S. Pat. No. 5,651,829 describes a process whereby the crystallization of maltitol in an atomizing apparatus is made possible, but only provided that very specific process conditions are met. Thus, the maltitol concentration of the maltitol syrup must be at least 92%, the syrup must be sprayed onto a moving pulverulent bed having a similar maltitol concentration and having a mass which is at least twice that of the syrup. The resulting product comprises crystalline maltitol microparticles agglomerated with each other.

Xylitol is commercially produced from xylan obtainable from various vegetable sources. It is the sweetest of the polyols and is extensively used in confectionery, dietetic foods, oral hygiene products and in pharmaceuticals. It is not only non-cariogenic but also exhibits anti-cariogenic properties, which makes its use, for instance in tooth paste, hard candy and chewing gum very desirable. Xylitol provides a pronounced cooling effect when it dissolves in the mouth and this is appreciated in many applications.

Xylitol has a solubility of 63 (w/w) in water at 20° C. and it crystallizes from aqueous solutions into crystals melting at 92 to 96° C. Crystalline xylitol exhibits a higher hygroscopicity than maltitol and in solution it has a lower viscosity than maltitol at the same concentration.

Crystalline xylitol is conventionally produced by crystallization from aqueous solutions. Crystallization of xylitol from aqueous solutions requires a high xylitol purity of the solution in order to provide acceptable crystals (see U.S. Pat. No. 4,066,711). Thus, complex chromatographic methods have been employed for providing a sufficient purity of the solution. Xylitol has also been melt crystallized from substantially water-free melts as described in JP 7416929 and subsequently also in U.S. Pat. No. 5,139,795. The obtained crystals may be milled to a powder before use.

Xylitol has also been produced in microcrystalline form as described in WO 99/59426 by contacting a xylitol solution with gas suspended solid xylitol particles, allowing microcrystallization to proceed and recovering a porous agglomerated microcrystalline xylitol product.

Lactitol is a polyol with a mild sweetening capacity and a low cooling effect compared to xylitol. In recent years lactitol has gained wide acceptance in confectionery, dietetic foods and pharmaceuticals such as in chocolates and mild laxative preparations.

Lactitol was for a long time considered impossible to crystallize properly. This is partly due to the great variety of lactitol forms which may crystallize out of an aqueous solution. Thus, there exist at least two anhydrous forms of lactitol melting at 121-123° C. and 146-152° C., respectively, at least one monohydrate melting at 90-100° C., at least one dihydrate melting at 72-75° C. and at least one trihydrate melting at 38-45° C. Lactitol is further capable of crystallizing in a variety of random lactitol-water structures and it also solidifies in amorphous form. Crystallization of lactitol from an aqueous solution requires a high lactitol purity of the solution in order to provide a stable crystalline product. The specific conditions for crystallizing each one type of lactitol in pure form are known today and are described in WO 98/39350.

Lactitol has also been produced in microcrystalline form as described in WO 99/47532. Reference is also made to EP 832 899.

In the prior art there are also disclosed some polyol products containing one or more of the present polyols, maltitol, xylitol and/or lactitol.

U.S. Pat. No. 5,017,400 describes a physical combination of milled crystalline xylitol and maltitol to provide a sweetener mixture with improved taste properties.

FR 2786665 describes a hard fondant containing vegetable oil or fat and a mixture comprising maltitol and xylitol.

U.S. Pat. No. 5,045,340 describes a hard confectionery containing xylitol and maltitol or lactitol. The sweets are produced by melting a mixture of xylitol and maltitol or lactitol and adding powdered xylitol to the cooled mixture under agitation.

U.S. Pat. No. 6,165,511 describes a polyol composition obtained by co-spray drying of at least two polyols. The process requires that at least 80% by weight of the product is a non-hygroscopic polyol, which according to the examples is always mannitol. Mannitol is known for its very low hygroscopicity and extremely low solubility and therefore it is easy to spray dry.

U.S. Pat. No. 5,958,471 describes a polyol composition obtained by co-spraydrying a mixture consisting essentially of sorbitol, xylitol and mannitol dissolved in water. The content of sorbitol in the mixture is 70 to 98%.

U.S. Pat. No. 5,376,389 describes a dual coating of xylitol and another polyol wherein the polyols are sprayed as sequential layers on the surface of chewing gum pellets. The dual coating is said to provide improved coating quality compared to a conventional xylitol coating.

WO 99/18935 describes a directly moldable tabletting aid containing more than 90% by weight of xylitol and less than 10% of another polyol. The tabletting aid is obtained by co-spraydrying or co-granulation of the polyols.

U.S. Pat. No. 5,580,601 describes a grainy confectionery product containing maltitol or xylitol in crystalline form. Small powdered crystals of the respective polyol are mixed into a cooked mass of solubilized polyol to provide a soft and grainy sweet with a water content of 3 to 20%.

Although the prior art includes a vast number of documents describing the crystallization of the present polyols on their own, and even some documents in which mixtures of polyols are provided, it is evident that especially the crystallization of xylitol, maltitol and lactitol poses special problems which makes crystallization complicated.

The polyols have a high solubility and the products produced by spray drying especially of solutions containing impurities have been sticky and instable. A typical example of this can be found in the spray drying of maltitol, where the prior art requires a maltitol concentration of above 92% (U.S. Pat. No. 5,651,829) in order to avoid undue stickiness and to obtain a satisfactory crystal by fluidizing. Stickiness is typically also due to enclosed water and amorphous products, both problems being well known from the crystallization of maltitol and lactitol.

Maltitol, xylitol and lactitol all require very high purity of their aqueous solutions for satisfactory conventional crystallization. Imperfectly crystallized polyols tend to be hygroscopic, which easily leads to instability during storage. It has not been possible to satisfactorily crystallize the individual polyols from aqueous solutions containing impurities, such as other polyols, in amounts as high as 25%.

Thus, combinations of the polyols have generally been made by physically mixing pure crystals of the separate polyols.

However, in the context of the present invention it has surprisingly been found that the polyols do not require the same purity for satisfactory microcrystallization according to the present invention. The present microcrystalline polyol compositions are obtained from solutions having a very high amount of "impurities", i.e. from solutions containing at least 25% of another polyol.

The polyols useful for providing the polyol composition of the present invention may naturally be purified individually before being used in the preparation of a liquid feed polyol mixture. However, it is one of the advantages of the present invention that such purification is not necessary and that crude polyol mixtures may be used as the starting material.

An object of the invention is to provide a product which avoids the drawbacks of the prior art and which provides a non-cariogenic polyol composition of maltitol, xylitol and/or lactitol in an intimately mixed ready-to-use form.

It is an object of the invention also to provide a stable and homogeneous pre-mixture of two or more polyols which mixture has a desired content of each of the polyols in the mixture and wherein there is no separation and/or fractionation of the polyols within the composition itself.

It is an object also to provide a stable polyol composition which is substantially non-hygroscopic and free-flowing.

It is an object of the present invention to develop a polyol composition having the desired sweetening capacity, cooling effect, laxative effect, non-cariogenic or anti-cariogenic effect etc., in other words, a composition having the desired properties of each of the polyols in the composition. By including the polyols in one and the same composition it is possible to avoid the need for separate mixing of the various component polyols at the point of use. The intimately mixed polyols in the homogeneous composition are not subject to separation and/or segregation.

An object of the invention is also to provide a novel granular polyol composition which is suitable for use in the confectionery as well as in the food and pharmaceutical industry. An object of the present invention is also to provide an improved process for the crystallization of polyol composition(s).

Another object of the present invention is to provide a particulate polyol composition product in a process which transforms a polyol solution into a solid polyol composition product in one overall operation.

An object is also to provide a process having a fast over-all operation. The process provides crystallization of the polyol solution in a significantly shorter time than conventional crystallization. Thus, the present microcrystallization process lasts only seconds in the air while a standard aqueous crystallization lasts for hours, mostly tenths of hours.

An advantage of the present invention is that it provides a non-cariogenic sweetening composition wherein maltitol and/or lactitol benefit from the anti-cariogenic properties and higher sweetness of xylitol.

A further advantage of the invention is that it provides a non-cariogenic sweetening composition wherein the pronounced cooling effect of xylitol, which is, for instance not desired in chocolates, is reduced by maltitol and/or lactitol.

An advantage is also that it provides a non-cariogenic sweetening composition wherein the burning aftertaste, which is felt in some cases when xylitol is used as the sole sweetener, is reduced by maltitol and/or lactitol.

SUMMARY OF THE INVENTION

It has now been surprisingly found that a stable and non-sticky crystalline polyol product can be obtained by combined microcrystallization of at least two of the polyols maltitol, xylitol and lactitol. The present invention is defined in the appended claims.

The present invention thus provides a microcrystallized polyol composition comprising at least two polyols, wherein said polyols are selected from the group consisting of maltitol, xylitol and lactitol and wherein said composition contains at least 25% by weight of each of at least two of said polyols microcrystallized together into a solid microcrystalline product.

The microcrystallized polyol composition is a solid product which comprises a porous granular composition of randomly agglomerated microcrystals containing maltitol, xylitol and/or lactitol.

Preferred compositions are provided by combinations of two of said polyols. Such combinations preferably contain from 25 to 75% by weight xylitol and from 75 to 25% by weight maltitol; from 25 to 75% by weight xylitol and from 75 to 25% by weight lactitol; or from 25 to 75% by weight lactitol and from 75 to 25% by weight maltitol. The preferred two-polyol compositions contain 30% or more of each of the two polyols and most preferably about equal amounts of the two polyols.

Combinations of all three polyols are also possible. In such a case, however, it is only required that two of them are present in at least 25% by weight, although it may be preferable that two of them comprise about 90% or more of the weight of the composition. A preferred three-polyol composition contains 30% or more of each polyol and most preferably about equal amounts of the three polyols.

Polyol compositions which include less than 25% of two of the present polyols are not included within the present invention. A proportion below 25% of the respective polyol is not large enough to impart the desired property to the composition.

The microcrystalline polyol composition of the present invention is essentially dry. This means that the free moisture content of the final product is below 1% and preferably below 0.5%, most preferably 0.05-0.5%. The composition may additionally contain crystal bound water especially in the form of lactitol hydrate crystals.

The preferred microcrystallized polyol composition according to the invention is substantially homogeneous and uniform and it consists essentially throughout its entire structure of a multitude of randomly agglomerated microcrystals containing two or more of said polyols microcrystallized together.

The invention also encompasses microcrystalline products having an inner core which differs from the microcrystallized outer portion. Such a core may comprise milled maltitol, xylitol and/or lactitol in the same ratio as the microcrystalline product or in some other desired ratio. The core may also comprise milled or microcrystalline particles of other polyols capable of functioning as cores for the microcrystallization of the present invention. Such polyols include mannitol, sorbitol, isomalt, erythritol, etc. Finally, the core may comprise inert or active ingredients which are coated by the microcrystals forming in the microcrystallization tower. Such ingredients include vitamins, minerals, colors, flavors, aroma compounds, pharmaceuticals, etc.

The microcrystallization process of the present invention is a fluidized microcrystallization wherein a liquid feed of at least two dissolved polyols is sprayed into contact with a dry feed of polyol crystals suspended in a gas, said spray wetting the surface of the dry feed. The solvent of the liquid phase is transferred into the gas phase by evaporation. This causes microcrystallization of the dissolved polyols on the dry feed polyol particles. The resulting microcrystallized polyol composition particles are, in a preferred embodiment of the invention, collected on an inert surface to form a porous agglomerated powder layer. The composition is then conditioned to provide a solid randomly agglomerated microcrystalline polyol composition. The ratio of the two or three polyols in the feeds is such that the resulting microcrystalline composition contains at least 25% by weight of each of at least two of the polyols.

DETAILED DESCRIPTION OF THE INVENTION

The polyol composition of the present invention includes at least 25% by weight of each of two polyols selected from maltitol, xylitol and lactitol, which means that the microcrystallizing polyol solution contains at least 25% by weight of a first and a second polyol. The second polyol comprises an "impurity" from the point of view of crystallization of the first polyol. Despite the presence of this "impurity" the polyols surprisingly crystallize into a stable, non-sticky microcrystalline composition which contains the polyols in a substantially uniform mixture throughout the whole of the product.

The microcrystalline polyol composition is a stable and homogeneous product and no separation or segregation of the polyols can take place within the mixture.

The microcrystallized character of the polyol composition makes it especially well suited for various end uses. Thus, the porous particles can be provided in various sizes, from a few millimeters to a few micrometers. Only a mild crushing is needed to break the product at the crystal faces. The microcrystalline structure further makes the product directly compressible into tablets. In contrast to this, a physical mixture of corresponding milled polyol crystals is not directly compressible.

The microcrystalline character of the polyol composition, which is essential in the invention, is provided by the production process.

In a preferred embodiment of the invention an aqueous solution of the polyols is brought into contact with fluidized particles containing microcrystalline polyols, the wetted particles are dried in a flow of warm gas, and the polyols on the surface of the particles are allowed to form new microcrystals on said surface.

The fluidizing microcrystallization used for producing the present polyol compositions ensures that the main crystallization takes place while the particles are in a fluidized state, i.e. suspended in an inert gas. As the polyol solution, which is sprayed onto solid polyol particles suspended in the gas stream, dries, the polyols in the solution crystallize as minute microcrystals on the particle surfaces. At the same time the wetted particles contact each other in the gas stream and adhere to each other forming bigger particles by a random agglomerization of smaller particles. The crystallization in the process is extremely fast and the solution is transformed from a liquid into a solid in a matter of seconds. The drying particles may be collected so as to form a porous agglomerated layer which, when dry, is brittle in the sense that it easily breaks at the interfaces between discrete microcrystals bridging two adhered particles.

The conditioning of the porous layer allows the microcrystallization to proceed for a sufficient time to provide a final product consisting substantially of a microcrystalline polyol composition. Although the conditioning takes longer than the microcrystallization, the overall crystallization from liquid to final solid is fast. The process typically takes from half an hour to two hours while a conventional crystallization typically lasts for tens of hours.

In a preferred embodiment of the invention the wetted particles are substantially dried while falling down with a co-current air stream and allowed to settle forming a porous layer of agglomerated microcrystallizing polyols. This layer is then conditioned and cooled. The microcrystallization conditions are selected so that the cooled layer is dry, porous and brittle. If desired, the layer may be broken up into smaller fractions.

In another embodiment of the invention the particles are retained in a suspended state in a stream if an inert gas such as air, nitrogen or carbon dioxide, while additional polyol solution is sprayed onto their surfaces until the particles have grown to a predetermined size or weight or have combined with other particles to said size or weight. The particles are then removed from the gas stream, e.g. by gravity and conditioned as described above.

The gas suspended dry feed is preferably provided by recirculating a portion of the microcrystallized product produced in the process itself. Said particles may comprise dust entrained in circulating drying air or it may be dust or fine particles provided by the crushing of the agglomerated microcrystallized mass. At start-up, in the absence of microcrystalline polyol composition, the solid dry feed of the process may comprise milled crystalline polyols from another source. This solid feed may, however, be progressively replaced by recycling part of the microcrystallized product, in order to provide a total or in any case a substantial microcrystalline structure throughout the product. The size of the dry feed particles is generally below 200 µm, preferably below 100 µm.

The liquid feed and/or the dry feed may contain a minor portion of an excipient, an active or inert ingredient and/or other sweetener than maltitol, xylitol or lactitol. Thus, the dry feed may, for instance, comprise a powder containing a core material selected from the group consisting of milled crystals of said at least two polyols, milled crystals and/or microcrystals of another polyol, milled crystals, microcrystals and/or powders of other inert or active ingredient(s).

In the present specification and claims the term "microcrystallization" and "microcrystallized" is to be understood as indicating a fluidized microcrystallization, i.e. the crystallization of the dissolved components of a liquid which is fluidized or suspended as minute droplets in a gas during the main crystallization procedure. The fluidizing gas evaporates the solvent component of the liquid and the mixture of solid components form minute microcrystals in the fluidized state.

The fluidizing technique used to produce the polyol composition provides unique characteristics to the product which are not obtainable by mixing milled polyol crystals nor by melt crystallizing from a molten polyol mixture. The fluidized microcrystallization provides a porous product wherein the microcrystals are relatively loosely bound to each other. This makes the product suitable for direct compression into tablets. It also facilitates the dissolution of the product. The product is stable and homogeneous, non-hygroscopic and free-flowing and it does not segregate into its separate components.

The terms "microcrystalline" and "microcrystal" as used throughout the present specification and claims should be understood to mean very small crystals produced by the above fluidized microcrystallization technique and having a size which on an average is below 50µ. The crystals generally have a size in the order of about 5 to 10µ, on an average, or even less. In contrast to the present microcrystals, the crystals obtained by polyol crystallization and recovered by filtration and centrifugation from liquid suspensions by prior known crystallization techniques are discrete crystals the particle size of which, on an average, is of the order of about 100-1000µ or larger.

The term "conditioning" used in the present specification and claims denotes a procedure whereby microcrystallized particles which still retain a certain amount of free solvent and hence also a small portion of dissolved or amorphous polyol contained therein, is kept in conditions which promote evaporation of the free solvent leading to substantially total solidification of the polyols. The conditioning proceeds more quickly at a slightly elevated temperature. However, the temperature should always be kept well below the melting range of the polyols. The conditioning also typically includes finally bringing the product to ambient conditions.

The term "free solvent" indicates solvent which is not bound in the crystal structure. The solvent may be any suitable inert and non-toxic solvent such as water or an alcohol. The preferred solvent is water and, for instance, the crystal bound hydrate water of lactitol monohydrate or dihydrate is not to be confused with the free water or free moisture of the product.

Of the polyols useful in the present invention, xylitol and maltitol are commonly known only to form anhydrous crystals, while lactitol may form crystals in the anhydrous, monohydrate, dihydrate or trihydrate forms. The conditions of the microcrystallization determine which lactitol crystal will be formed. At higher temperatures, the anhydrous form is predominant, while lower temperatures favor the formation of monohydrate and dihydrate. The trihydrate is less stable and generally transforms into one or the other of the crystal forms. Due to the high supersaturation and the high proportion of "impurities" in the microcrystallizing liquid, mixtures of anhydrous lactitol and lactitol monohydrate may be formed.

Further, all of the polyols are capable of solidifying in amorphous form and amorphous polyol mixtures may thus be included in the mixture. The crystal mass may thus include amorphous maltitol, xylitol and/or lactitol up to about 20%, more generally less than 15% and preferably less than 10% by weight.

The polyol compositions of the present invention form a thorough and intimate mixture wherein the different polyols cannot be distinguished visually. Still, it has been found that the compositions contain in each microcrystal the individual crystalline forms of the different polyols. Thus, tests performed by X-ray diffractometry and differential scanning calorimetry (DSC) have revealed that the polyols in the composition typically do not form true co-crystals i.e. crystals having a joint crystalline structure distinguished from that of the individual polyols.

However, it has been found that the microcrystals of a substantially equimolar mixture of maltitol and xylitol form an eutectic mixture having a melting point different from that of the individual polyols. Thus, maltitol melts in the eutectic mixture with xylitol already at about 90° C. (the normal m.p. of maltitol is 148-151° C.). This allows use of molten maltitol at a significantly lower temperature than without the eutectic mixture. The lower temperature may be utilized in hard candies, in melt granulation and in contact with any such ingredients which are heat sensitive and which cannot be subjected to the higher melting point of pure maltitol. The composition also has a lower melting enthalpy than the combined value for crystalline xylitol and maltitol.

The microcrystallized polyol composition may be used as such as obtained directly from the process, it may be broken up into granules or milled into a powder or it may be cast into a desired form. The product may be crushed, milled and/or classified e.g. by sieving to provide a product of a desired size and size distribution.

Although the size of the granules of the granular product obtainable according to the present invention is not critical and may vary according to the intended use of the product, the mean particle size of the polyol composition granules is generally between about 0.05 and 2.0 mm. The preferred mean particle size is generally about 0.1-0.4 mm. Each granule contains a mass of minute microcrystals. The particle size and particle distribution of the granules may be controlled to suit the intended use.

The microcrystallized polyol composition according to the present invention may be used as a bulk or special sweetener for the total or partial replacement of sucrose or other sweetening agents. Thus, it is useful in dietetic products, in confectionery, bakery products, cereals, desserts, ice cream, jams, beverages, etc., especially in chocolate, marzipan, chewing gum, hard candy and granulated or tabletted table top sweeteners. It is also useful in oral hygiene products such as tooth paste and mouth rinses.

The polyol composition according to the present invention is also useful in pharmaceuticals where it is preferably included as a sweetener, an excipient, a diluent and/or a carrier. The polyol composition may also be used as an active ingredient, e.g. to provide an anticariogenic effect by xylitol or a laxative effect by lactitol. The microcrystals containing product according to the present invention can be directly compressed into a tablet.

Even though in some situations the microcrystalline nature of the polyol composition may be lost during the end use, for instance, by dissolving in a dough or melting in a candy, the present polyol composition offers the advantage of providing an intimate mixture of two or three desirable non-cariogenic sweeteners. The product comprises a non-segregating premixture which is much easier to use than having to mix different polyols for each recipe.

A preferred embodiment of the present invention relates to a special non-cariogenic sweetener which comprises a microcrystalline polyol composition. Such a sweetener may include other components such as excipients, binders and/or other sweeteners.

Such other sweeteners are preferably also non-cariogenic sweeteners such as intense sweeteners taken from the group comprising dipeptide sweeteners, saccharin, acesulfame K, aspartame, alitame, stevioside, cyclamate, sucralose and neohesperidin dihydrochalcone, etc.

The preferred non-cariogenic sweetener according to the present invention consists essentially of a microcrystalline maltitol/xylitol composition.

Other components which may be used in the sweetener and/or other applications such as in pharmaceutical preparations may comprise, for instance, microcrystalline cellulose, carboxymethyl cellulose, polydextrose, dextrose, maltodextrin, lactose, sugar, fructose, glucose, lactose, mannitol, sorbitol, erythritol, isomalt and the like.

The liquid feed used in the microcrystallization process of the present invention generally comprises a solution containing the two or three polyols dissolved in water at a total concentration of about 60-90% on DS. In an alternative embodiment the individual polyols are sprayed simultaneously as separate solutions onto the dry feed particles. The separate solutions may be sprayed intermittently and/or successively into the tower. However, in this situation it is more difficult to ascertain that the resulting product is homogeneous.

The microcrystal containing polyol composition may also be microcrystallized with other compounds. Thus, if the solid and/or liquid feeds comprise other components, such as one or more of the above mentioned sweeteners or excipients, binders, active or inert ingredients, etc. the product discharged from the microcrystallization apparatus will contain said other component(s) integrally in its structure. A secondary or tertiary spray of another solid or liquid component may also be fed into the microcrystallization apparatus into contact with the microcrystallizing polyol composition(s).

Only such additional components can be used which do not significantly and adversely interfere with the microcrystallization according to the present invention. Specifically, it is necessary that the additional components and the amounts thereof are selected so that the microcrystallizing particles will be substantially dry by the time they leave the suspended state. If the initially dried particles contain too much moisture, they will be clogged together forming large hard compact structures, wherein the microcrystallization throughout the product cannot be ensured, the product may be unstable and hygroscopic and crushing of the product to provide free-flowing granules may be difficult.

Further embodiments of the present invention relate to the use of the polyol composition as such or in the production of useful end products. Such products are typically edible products, pharmaceutical products and/or oral hygiene products such as those mentioned above. The microcrystalline polyol composition of the present invention may, for instance, be advantageously used in the production of chocolate and chewing gum or in bakery products.

The present invention will now be described in greater detail. This description should, however, not be taken as limiting the invention to the precise wording thereof. A person skilled in the art will be able to provide numerous modifications and variations of the process without deviating from the invention as defined in the appended claims.

The microcrystalline polyol composition granules produced according to the present invention are shown in the accompanying drawing, wherein FIG. 1 is a SEM photo showing a microcrystalline maltitol/xylitol composition structure in 400× magnification.

Figure 2:
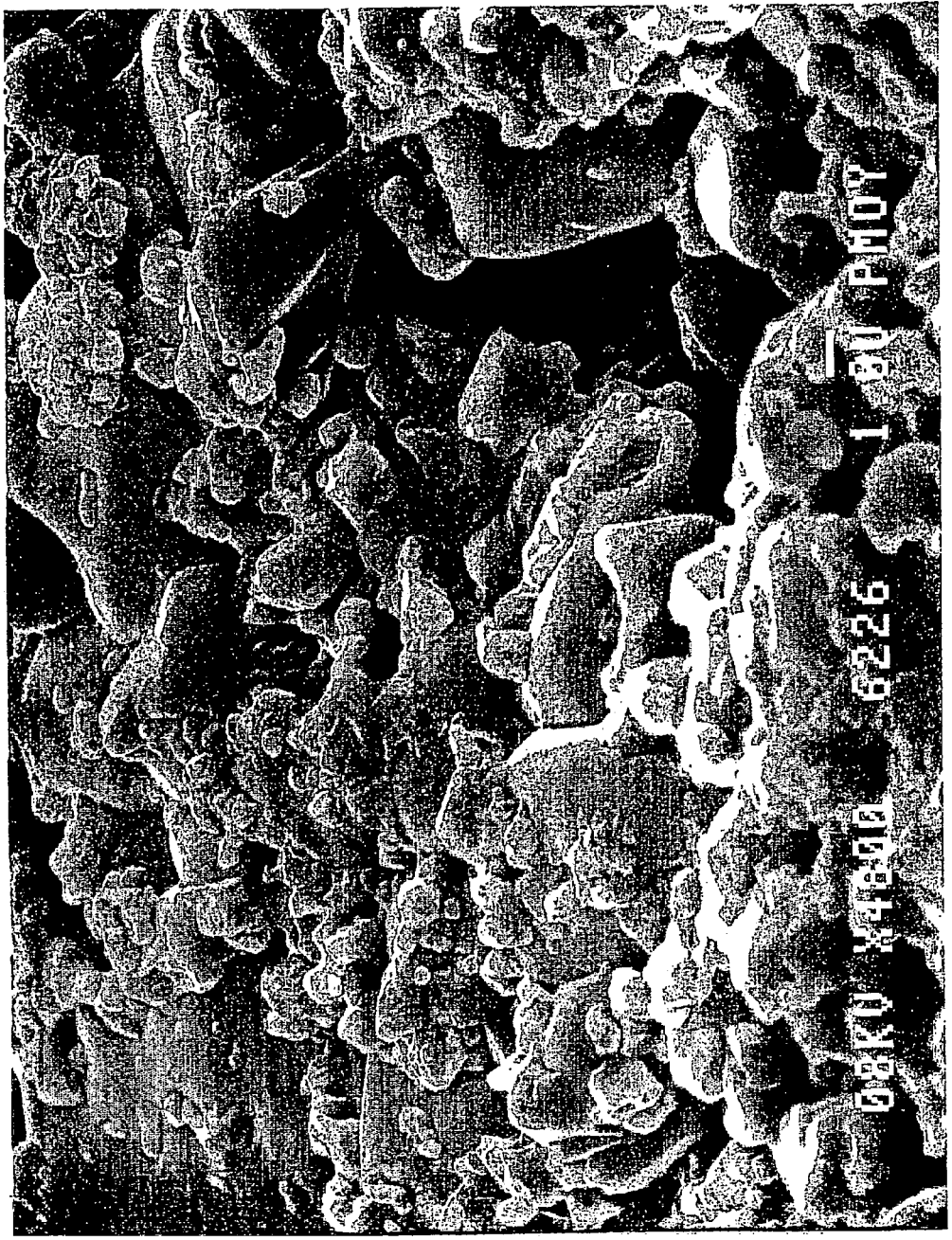

FIG. 2 is a SEM photo showing the structure of FIG. 1 in 4800× magnification.

In the preferred fluidized microcrystallization process according to the present invention a liquid containing dissolved polyols is provided. The solvent component of said liquid is preferably water, although the polyols may also be microcrystallized from other solvents such as alcohols, e.g. ethanol or isopropanol.

The total polyol concentration of an aqueous feed solution containing the two or three polyols should preferably be over 50% on DS (dry substance) in order to quickly provide supersaturation for the crystallization. Said concentration is preferably about 60-90% on DS, preferably 60-80% on DS.

Prior to feeding the solution into a microcrystallization apparatus, the solution is preferably heated in order to facilitate the subsequent removal of the solvent component and in order to more quickly provide suitable crystallization conditions in said apparatus. The temperature and concentration of the solution as well as the amount of gas in the apparatus should be selected so as to allow the solvent to evaporate during the gas-suspended crystallization at the microcrystallization temperature. Taking into account that the crystallization of the present polyols frees energy and the evaporation consumes energy, the energy balance should be such that it provides an optimum crystallization temperature and a sufficient evaporation of the solvent. The product landing on the bed should not be molten or wet.

The solution should be distributed in the form of very small droplets in the microcrystallization apparatus. To this end, the solution is preferably atomized at a pressure through a nozzle into said apparatus.

The atomized solution is brought into contact with fluidized or gas suspended solid polyol particles, preferably recirculated microcrystalline polyol particles from the process itself. Most preferably a fine fraction of the product is recirculated. Such a fine fraction typically has a mean particle size below about 0.2 mm, preferably below about 0.1 mm. However, when larger individual product particles are desired, correspondingly larger polyol particles may be recirculated or fed into the apparatus from another source. The dry solid particles may also be dust or fine particles entrained in the drying air and fed back into the apparatus as solid feed.

The solution is generally contacted with the gas suspended solid particles in an upper portion of the microcrystallization apparatus. Here the wetted particles and any free droplets of polyol composition solution meet a drying gas such as heated air which is introduced into the apparatus to provide removal of the solvent component of said solution. The evaporated solvent is removed from the apparatus together with the drying gas.

The drying should be accomplished in such a way as to substantially remove the solvent while said polyol composition material is still in a gas suspended state. When the solvent is water, said drying should provide a suspended polyol composition dried to a free moisture content of about 3 to 0.5%.

In case the drying is not sufficient or too much liquid has been fed into the apparatus, in other words, if the energy balance is incorrect, the polyol composition will be too wet and the crystals will stick together to form a dense or syrup-like structure where separate microcrystals can no longer be properly discerned. Too much energy, on the other hand may prevent crystallization or may even melt the crystals.

A substantial amount of solid polyol composition feed is required in order to obtain a satisfactory particulate microcrystalline product. The suitable ratio of liquid polyol composition feed to solid polyol composition feed varies with the microcrystallization conditions. The ratio should be selected so as to provide a wetting of the solid particle surfaces without dissolving the core of the seed particles. A ratio of liquid feed to dry feed between 2:1 and 1:4, preferably between 1:1 and 1:2 on DS has been found most suitable in an aqueous system performed in a co-current system. The ratio can be changed provided that a correct energy balance is maintained.

The suspended wetted particles may be dried by a co-current or a counter-current stream of drying gas. The co-current gas will flow downwards with the falling particles while a counter-current gas stream will retain the particles in a gas suspended or fluidized state for a longer time. A horizontal or inclined gas flow may naturally also be used.

The particles carried downwards with a co-current gas stream in a microcrystallization apparatus should be substantially dry, i.e. the free moisture content should not exceed 3% by the time they reach the bottom portion of the apparatus and are allowed to settle there. The settling surface is preferably a means allowing building up of a suitable layer and for adjusting the residence time in the layer. A belt moving at a speed sufficient to allow build up of a porous agglomerated layer of polyol composition is generally suitable. The layer typically has a thickness of about 0.5 to 15 cm, preferably about 3-7 cm. The layer should preferably be so porous that gas easily penetrates therethrough.

The agglomerated layer of solidified polyol composition should further be conditioned so as to allow microcrystallization to proceed in the layer. Said conditioning preferably includes two or more separate steps or phases with different temperatures. The layer is preferably treated e.g. by blowing a hot drying gas therethrough. The temperature, relative humidity and amount of the drying gas is selected so as to provide suitable microcrystallization conditions in the layer.

The microcrystallized particles are generally conditioned at a temperature of about 40-90° C., preferably about 65-72° C., most preferably about 67-70° C. to a free moisture content below 1%, preferably about 0.05 to 0.5%.

The conditioning may preferably be performed in several successive steps with a suitable temperature profile of the drying gas so as to ensure a proper drying and microcrystallization of the polyol composition. The conditioning should continue for a sufficient time to allow microcrystallization of any liquid polyol to take place in the layer.

When microcrystallized polyol composition is recirculated within the process, care should be taken to recirculate only essentially dry particles. Problems may occur if the dry feed comprises recycled material which is moist. The microcrystallized layer should thus be properly dried before crushing and/or recycling.

If the surface on which the layer is allowed to settle is flat, the result will be a substantially flat porous and brittle plate comprising microcrystalline polyol composition. However, the microcrystallizing polyol composition may also be gathered in moulds having any desired form such as resembling ordinary sugar lumps, or bars, strings, cubes, etc.

When the microcrystal containing product is in the form of an agglomerated layer, it is generally desirable to break up the layer to provide discrete granules. Only a mild crushing action is normally required for breaking up the bonds between individual microcrystals.

The resulting microcrystal containing polyol composition granules may be milled and fractionated and a portion of the fines may be recirculated to provide the dry feed into the microcrystallization apparatus.

Generally the microcrystalline polyol composition layer is broken up so as to provide granules having a mean particle size of about 0.05 to 2.0 mm, preferably about 0.1-0.4 mm.

In the case where the drying air is blown counter-currently to the downward movement of the wetted particles in the microcrystallization apparatus, the particles will be fluidized therein. By a suitable fluidization action the particles will be made to recirculate within the apparatus. In the apparatus a simultaneous wetting, drying and microcrystallization of particles will take place. Each particle will pass through several wetting and drying/microcrystallization stages, colliding with other particles and growing ever bigger until the particle reaches the size and weight wherein the fluidizing air no longer manages to retain them in a fluidized state. At this stage the particles will fall to the bottom of the apparatus and may be removed therefrom to be conditioned, for instance as described above.

The solid feed to the microcrystallization apparatus in the counter-current case preferably comprises dust and fine particles recovered from the circulation of the drying air.

In the granular microcrystalline polyol composition according to the present invention each granule substantially throughout its entire structure comprises a multitude of microcrystals of polyol composition agglomerated together in a random manner.

The microcrystals in each product granule of the present invention are individually very small compared to the crystals formed by prior art crystallization processes. Generally, the size of the microcrystals in each particle is on an average below 50µ, preferably about 5-10µ on an average.

The invention will now be illustrated with the aid of a few examples. These examples should in no way be taken as limiting the invention.

EXAMPLE 1

Microcrystallization of Maltitol/xylitol 50:50.

Maltitol/xylitol liquid feed solutions were prepared by dissolving crystalline maltitol (C*Maltidex CH16385 produced by Cerestar, Krefeld, Germany; maltitol purity 99.7% on DS) into an aqueous xylitol solution (xylitol produced by Xyrofin Oy, Kotka, Finland; xylitol purity 97.1% on DS) to a total concentration of 67-73% on DS. The ratio of maltitol to xylitol was 1:1 by weight. The feed solution was heated to a temperature of 55-63° C. and filtered.

An initial dry feed mixture was provided by mixing milled crystalline xylitol with milled crystalline maltitol also in the ratio 1:1 by weight. After the initial phase (see Table 1; lines 1 and 2) microcrystallized maltitol/xylitol particles were recirculated as dry feed.

The tests were carried out with a Niro Filtermat FMD 6.3 apparatus. The warm solution was atomized by air into the top of the apparatus. The atomizing air was heated to 55-75° C. and the walls of the apparatus to 40-50° C. The atomized droplets landed onto the surface of dry feed powder fed to the atomizing nozzle area. The feed ratio of liquid to dry feed is indicated in Table 1. The partly dried droplets fell with a co-current laminar hot air stream fed through two separate inlets Pr1 and Pr2 at 550 kg/h and 200 kg/h, respectively, towards a moving belt at the bottom of the spray tower. An agglomerated porous powder layer was built up on the belt. The belt moved at variable speeds with the settled layer through two conditioning zones I and II feeding air at 200 kg/h and 250 kg/h, respectively. The air of the second zone was dehumidified prior to spraying.

The conditioned layer was conducted to a gyratory crusher and further to a rotating drying drum. The product was heated in the drum with dehumidified warm air. After the drum drying the product was dried in a fluid bed drier with dehumidified air at 40° C., whereafter the product was packed in bags.

The test conditions are indicated in Table 1.

TABLE 1

Microcrystallization conditions, X/M 1:1

| Liquid feed | | Dry feed | Feed* | Air temp. ° C. | | Condition ° C. | | |
|---|---|---|---|---|---|---|---|---|
| DS % | ° C. | type | ratio | Pr1 | Pr2 | I | II | Drum ° C. |
| 72.5 | 57-58 | Cryst. | 1:2.3 | 130 | 90 | 75 | 60 | 80 |
| 73 | 58-59 | Cryst. | 1:3 | 125 | 90 | 60 | 60 | 80 |
| 67 | 58-59 | Microcr. | 1:2.3 | 120 | 90 | 60 | 60 | 80 |
| 68 | 58-59 | Microcr. | 1:2.6 | 120 | 90 | 60 | 60 | 40 |
| 68 | 63 | Microcr. | 1:2.5 | 123 | 90 | 60 | 75 | 80 |

*The Feed ratio indicates the ratio of liquid to dry feed

EXAMPLE 2

Physical Properties of Microcrystalline Maltitol/xylitol

A batch of microcrystalline maltitol/xylitol produced in accordance with Example 1 (the last row in Table 1) was analyzed as to its physical properties.

The microcrystalline product melted at about the melting point of xylitol due to the eutectic behaviour of the maltitol/xylitol product. The melting behaviour was observed by DSC and no peak was noted at the maltitol melting point of 148-151° C.

The following analysis methods were used:

Moisture was measured using coulometric Karl Fischer titration

Density was measured with a densiometer

DSC analysis was made at a speed of 10° C./minute

Flowability: A 500 g sample was poured into a a dry funnel whose bottom opening was blocked. The bottom opening was unblocked and the time needed for the entire sample to flow out of the funnel was measured.

Bulk density: The sample was poured in a 1000 ml measuring cylinder. The sample was tapped 10 times, levelled and the amount of the sample was weighed.

Hygroscopicity: 10 g of the sample was weighed to a petri dish. The open dish was put into a humidity cabinet. The change in weight was measured. Climate cabin temperature was 25° C. and relative humidity 60%.

Particle size distribution: Sieve analysis was used to determine the particle size.

Dissolving rate: 100 g of the sample was put to 100 g of water at 20° C. A small paddle mixer, 250 rpm, was used to mix the solution. During the dissolution the refractive index was measured, and the time for dissolving was recorded.

The analysis results are shown in Table 2

TABLE 2

Maltitol/xylitol composition analysis results

| Analysis | Milled regular | Milled fine | Milled extra fine |
|---|---|---|---|
| HPLC $Pb^{2+}$, % on DS | | | |
| Xylitol | 49.1 | 49.0 | 49.3 |
| Maltitol | 49.6 | 49.6 | 49.7 |
| Others | 0.9 | 0.9 | 0.9 |
| Moisture, % | 0.22 | 0.20 | 0.19 |
| Flowability, s | 26 | no | no |
| Bulk density | | | |
| poured, g/l | 714 | 545 | 404 |
| tapped, g/l | 729 | 562 | 416 |
| DSC | | | |
| Onset, ° C. | 84.9 | 86.2 | 85.7 |
| Peak, ° C. | 89.0 | 89.3 | 89.1 |
| Enthalpy, J/g | 118 | 118 | 116 |
| Other peak, ° C. | 112.6 | 113.7 | 113.5 |
| Enthalpy, J/g | minimal | minimal | minimal |
| Sieve analysis | | | |
| Mean particle size, mm | 0.26 | 0.16 | 0.10 |
| Coeff. of variation, % | 39 | 39 | 42 |
| Pamas-particle size | | | |
| Mean particle size, microns | | 17.7 | 16.6 |
| Dissolving rate, min | 3.5 | 3.0 | 3.0 |
| Hygroscopicity | | | |
| Water sorption, % in 22 h | 0.68 | 0.53 | 0.56 |

The microcrystalline maltitol/xylitol in SEM photos in 400× magnification (FIG. 1) showed a myriad of small crystals looking like normal crystal lumps but smaller. The microcrystalline structure showed very clearly in 4800× magnification (FIG. 2).

EXAMPLE 3

Microcrystallization of Maltitol/xylitol 25:75.

About 500 g of a 50/50 mixture of milled xylitol and maltitol crystals were placed in an Aeromatic laboratory fluid bed dryer. Aqueous xylitol-maltitol solutions with a concentration of about 70% on DS and a xylitol to maltitol ratio of 75 to 25 were sprayed onto the crystals in the dryer.

The bed temperature in the dryer was 54 to 63° C. The spraying time was 4 minutes, after which the bed was dried at a constant temperature first at about 60° C. for about 5 minutes and then at about 65° C. for about 40 minutes. The procedure was repeated several times until a major portion of the product comprised microcrystals.

The resulting microcrystalline product had a uniform structure and a moisture of 0.08%. The melting behavior of the crystals was analysed with DSC. The heating was performed from 30° C. to 170° C. at 10° C./min. The microcrystals showed one peak at 93° C. and another very small peak at 148° C. This indicates that the maltitol microcrystals melted at a lower temperature due to the eutectic behaviour of the composition.

EXAMPLE 4

Microcrystallization of Maltitol/lactitol 50:50.

Maltitol/lactitol liquid feed solutions were prepared by dissolving crystalline maltitol (C*Maltidex CH16385 produced by Cerestar, Krefeld, Germany; maltitol purity 99.7% on DS) into an aqueous lactitol solution produced by dissolving crystalline lactitol (Lactitol CM 50 produced by Xyrofin Oy, Kotka, Finland) to a total concentration of 67-73% on DS. The ratio of maltitol to lactitol was 1:1 by weight. The feed solution was heated to a temperature of 55-75° C. and filtered.

An initial dry feed mixture was provided by mixing milled crystalline lactitol with milled crystalline maltitol also in the ratio 1:1 by weight. After the initial phase (see Table 3; row 1) microcrystallized maltitol/lactitol particles were recirculated as dry feed.

The tests were carried out with a Niro Filtermat FMD 6.3 apparatus. The warm solution was atomized by air into the top of the apparatus. The atomizing air was heated to 55-75° C. and the walls of the apparatus to 45-60° C. The atomized droplets landed onto the surface of dry feed powder fed to the atomizing nozzle area. The feed ratio of liquid to dry feed is indicated in Table 1. The partly dried droplets fell with a co-current laminar hot air stream fed through a nozzle Pr1 at 480 kg/h towards a moving belt at the bottom of the spray tower. An agglomerated porous powder layer was built up on the belt.

The belt moved at variable speeds with the settled layer through two conditioning zones I and II feeding heated air at 200 kg/h each. The air of the second zone was dehumidified prior to spraying.

The conditioned layer was conducted to a gyratory crusher and further to a rotating drying drum. The product was heated in the drum with dehumidified warm air. After the drum drying the product was dried in a fluid bed drier with dehumidified air at 40° C., whereafter the product was packed in bags.

The test conditions are indicated in Table 3.

TABLE 3

Microcrystallization conditions, M/L 1:1

| Liquid feed | | Dry feed | Feed* | Air temp. ° C. | Condition ° C. | | Drum |
|---|---|---|---|---|---|---|---|
| DS % | ° C. | type | ratio | Pr1 | I | II | ° C. |
| 68 | 65-75 | Cryst. | 1:1 | 170 | 75 | 80 | 40 |
| 68 | 70 | Microcr. | 1:1.2 | 175 | 70 | 70 | 40 |

*The feed ratio indicates the ratio of liquid to dry feed

EXAMPLE 5

Microcrystallization of Xylitol/lactitol 50:50

A continuous fluid bed xylitol/lactitol microcrystallization is performed in an apparatus having a fluid bed drying chamber, equipped with a spray nozzle system inside in the middle of the chamber. The apparatus comprises a bottom screen with a hole for the discharge of the heaviest particles, and a cyclone to recover light particles.

The chamber is loaded with 500 g of powdered xylitol and 500 g of powdered lactitol to act as initial seed material for the microcrystallization of the xylitol/lactitol composition. The powdered dry feed is fluidized with a flow of air (temperature 55-85° C.) through the bottom screen. A solution of lactitol (purity 99% on DS) and xylitol (purity 98.5% on DS) having a total concentration of 65% on DS at a temperature of 70° C. is fed into the chamber with a pump, atomized by means of a nozzle and sprayed over the fluidized powder.

The solution is supplied at a rate of 1 kg/h at a pressure of 1.5 bar to the fluidized dry powder. The air flow rate is adjusted to fluidize the polyol composition and to evaporate water at a rate sufficient to crystallize the polyol composition. A microcrystalline agglomerate is formed when the polyol solution crystallizes around the powder particles. The agglomerates remain in a fluidized state until they fall down when their weight is high enough. Microcrystallized polyol agglomerates are discharged continuously through the bottom opening.

In the drying chamber the lightest, non-agglomerated particles are removed from the top of the chamber entrained in the exiting air stream. This fine microcrystalline polyol material is recovered in a cyclone and fed back to the chamber to act as a continuous dry feed stream.

The discharged agglomerated product is conditioned at a temperature of 45-50° C. for 30 minutes to balance the microcrystallization.

Steady state conditions are reached when all the powdered xylitol and lactitol used as starting dry feed has been discharged from the process. The product obtained thereafter is a totally microcrystalline product which throughout its entire structure consists of a microcrystalline xylitol/lactitol composition.

EXAMPLE 6

Chewing Gum

A microcrystalline maltitol/xylitol product produced according to the process of Example 1 having a mean particle size of about 300 μm was evaluated in a standard stick chewing gum production and compared to a chewing gum made from a commercially available milled xylitol having a particle size wherein 90% was <100 μm.

The following ingredients were used:

| Ingredient | % Fresh Basis |
|---|---|
| Gum base, Nova Base (Dreyfus) | 25.0 |
| Sorbitol Syrup, Sorbifin LS (Xyrofin) | 7.2 |
| a) Milled xylitol (Xyrofin) | 55.0 |
| b) Microcrystalline maltitol/xylitol | 55.0 |
| Mannitol, milled (Cerestar) | 8.0 |
| Glycerine (Henkel) | 2.0 |
| Peppermint Flavour liquid (IFF) | 1.2 |
| Peppermint Flavour powder (IFF) | 1.6 |
| Aspartame (Nutrasweet) | q.s (0.05) |

The chewing gums were produced by placing half of the xylitol or the maltitol/xylitol powder, respectively, in a Z-blade mixer and mixing in the softened gum base at a mixer temperature of 40° C. The ingredients were thoroughly combined before the next ingredient was added. Then the sorbitol liquid was added followed by the remaining portion of the xylitol or the maltitol/xylitol, respectively, the mannitol and the powdered flavour.

The glycerin was combined with the liquid flavour and aspartame and added to the mixer. As soon as a homogeneous paste was formed, it was removed from the mixer and dusted with miffed mannitol. The paste was laminated to required thickness and cut.

The commercial crystalline xylitol gum processed well in about 11 minutes. The finished gum had a good chew and posed no problems during processing. The microcrystalline maltitol/xylitol gum processed slightly quicker, in about 8 minutes. The paste produced was very soft and the finished gum had a softer texture than the batch produced with the commercial crystalline xylitol. This can be attributed to the larger particle size of the material. No grittiness was detected when chewing the sample.

As can be seen from the above results the microcrystalline maltitol/xylitol is suitable for use in a stick chewing gum.

EXAMPLE 7

Hard Candy

Microcrystalline maltitol/xylitol product produced according to the process of Example 1 was evaluated in a standard hard candy production. The following ingredients were used Microcrystalline maltitol/xylitol
Crystalline Lactitol (Danisco Sweeteners)
Water
Acesulfame K (Hoechst)
Blueberry Flavour (DI 27328)
Citric acid (Bahrat Starch Industries, Ltd)

A mixture of 20% microcrystalline maltitolixylitol and 80% lactitol was diluted with water and placed in a sauce pan. The batch was first heated on a hot plate until all the material was solubilized. The batch was then transferred to a vacuum cooker and heated further. The blend formed a sticky mass even at a relatively low temperature. The syrup was then transferred from the cooker to a slab and tempered until a suitable texture for drop rolling was achieved. The tempered mass was fed through a drop roller. The candies once stamped were of an acceptable quality.

EXAMPLE 8

Pectin Jellies

Microcrystalline maltitol/xylitol product produced according to the process of Example 1 was evaluated in a standard pectin jelly production.

The following ingredients were used
Microcrystalline maltitol/xylitol
Pectin (CF 120) (Danisco Ingredients)
Water
Sodium citrate
Citric acid (Bahrat Starch Industries, Ltd)
Litesse Ultra® 70% soln (Danisco Sweeteners)
Raspberry Flavour The above ingredients were worked into a jelly according to a standard pectin jelly recipe previously used for crystalline xylitol. The microcrystalline maltitol/xylitol formed an acceptable jelly with a good elasticity.

EXAMPLE 9

Chocolate

A mixture of microcrystalline maltitol/xylitol produced according to the procedure described in Example 1 was assessed in a standard chocolate production.

The following ingredients were used

| | |
|---|---|
| Microcrystalline maltitol/xylitol | 46.0% |
| Cocoa Liquor (BCM) | 42.0% |
| Cocoa Butter (BCM) | 11.8% |
| Lecithin (Lucas Myer) | 0.2% |

The sweetener was mixed with the cocoa liquor. The resulting mixture was then passed through a three roll refiner to produce a flake. The flake was mixed again and a part of the cocoa butter was added. The mix was re-refined with increased pressures to produce a flake with a fat content of 32%. The resulting flakes were stored prior to conching.

The batch of flake was heated to 40° C. This temperature heated the flake sufficiently for ease of processing without over-heating. The batch was loaded into a conch and the remaining cocoa butter was added to produce a final chocolate with 35% fat. All lecithin was added one hour prior to removal of the batch from the conch.

The chocolate produced with microcrystalline maltitol/xylitol had a lower cooling effect than chocolate produced with standard xylitol.

EXAMPLE 10

Madeira Cake

A mixture of microcrystalline maltitol/xylitol produced according to the procedure described in Example 1 was assessed in a standard madeira cake production.

The following ingredients were used

| | |
|---|---|
| Heat-treated cake flour | 22.53% |
| Microcrystalline maltitol/xylitol | 20.73% |
| Egg, fresh, whole | 18.03% |
| Water | 15.72% |
| High ratio fat | 13.52% |
| Litesse$^R$ II | 5.21% |
| Skimmed milk powder | 1.60% |
| Spray dried egg albumen | 1.10% |
| Baking powder | 0.90% |
| Salt | 0.60% |
| Acesulfame K | 0.06% |

The liquid ingredients were mixed in a bowl and then the dry ingredients were added followed by the fat. Mixing was performed on speed 1 for 30 seconds, and the dough was scraped down. Thereafter mixing was continued on speed 2 for 1.5 minutes and the dough was scraped down. Mixing on speed 2 was continued for 1.5 minutes more until the relative density was 0.70-0.75. The dough was deposited in paper cases containing 300 g each and baked in an oven at 200° C. for 30 minutes. The finished cake had a good quality both in texture and in flavour.

EXAMPLE 11

Packaging Test

Microcrystalline maltitol/xylitol 50:50 produced in a Niro Filtermat FMD 6.3 pilot plant in accordance with the procedure described in Example 1 was tested for stability at packaging. Three package types were used. These comprised two bags and one box. The bag and box layers were as follows: One bag had three paper layers and one PE layer of 0.076 mm thickness; the other bag had three layers of paper and one PE layer of 0.120 mm thickness; and the cardboard box had an internal plastic bag of LDPE of 0.120 mm thickness.

The microcrystalline material was loaded into the bags and boxes and the packages were carefully closed and stored without piling to avoid putting pressure on the material. The bags were stored for three months and they were checked visually and manually twice during the test time.

The test showed that the microcrystalline maltitol/xylitol remained free-flowing during the whole of the test period in all tested packaging materials.

The invention claimed is:

1. A process for the microcrystallization of xylitol and maltitol into a polyol composition, comprising the steps of:
   (a) spraying a liquid feed of dissolved xylitol and maltitol containing at least 30% by weight of each at the dry solids concentration of 60-90% into contact with a gas suspended dry feed of small crystals containing xylitol and maltitol so as to wet the surface of said dry feed particles with said liquid feed, wherein the ratio of liquid feed to dry feed is between 2:1 and 1:4;
   (b) evaporating the solvent of said liquid feed causing microcrystallization of said dissolved xylitol and maltitol on said dry feed particles and drying in the gas suspended state to a free moisture content of 0.5-3%; and
   (c) conditioning the microcrystallized particles at a temperature of 40-90° C. to provide a solid randomly agglomerated microcrystalline xylitol-maltitol composition with microcrystals of 5-10 micrometers in size, a free moisture content of 0.05%-0.5%, and that which melts at about 90° C.;
   wherein the ratio of xylitol and maltitol in said feeds being such that the resulting microcrystalline eutectic mixture contains 30% or more of each of xylitol and maltitol microcrystallized together into a solid microcrystalline product;
   (d) optionally milling the dried randomly agglomerated microcrystalline polyol composition from step c) to a mean particle size of 0.1-0.4 mm.

2. A process according to claim 1, wherein said liquid feed comprises a solution containing xylitol and maltitol dissolved in water at a total concentration of about 60-90% on dry substance (DS).

3. A process according to claim 1, wherein said liquid feed comprises separate solutions of xylitol and maltitol dissolved in water, said separate solutions being simultaneously sprayed onto said dry feed particles.

4. A process according to claim 1, wherein said liquid feed comprises separate solutions of xylitol and maltitol dissolved in water, said separate solutions being separately and intermittently sprayed onto said dry feed particles.

5. A process according to claim 1, wherein the dry feed comprises recirculated microcrystallized polyol composition milled and/or sieved to a particle size of less than 200 µm.

6. A process according to claim 1, wherein the dry feed comprises recirculated microcrystallized polyol composition milled and/or sieved to a particle size of less than 100 µm.

7. A process according to claim 1, wherein the ratio of liquid feed to dry feed is between 1:1 and 1:2 on DS.

8. A process according to any one of claims 1-7, wherein said liquid feed and/or dry feed contains a minor portion of an excipient, an active or inert ingredient and/or sweetener other than maltitol or xylitol.

9. A process according to claim 1, wherein the dry feed comprises a powder containing core material selected from the group consisting of milled crystals of xylitol and maltitol, milled crystals and/or microcrystals of another polyol, and milled crystals, microcrystals and/or powders of other inert or active ingredient(s), said core material being milled and/or sieved to a particle size of less than 200 µm.

10. A process according to claim 9, wherein said core material is being milled and/or sieved to a particle size of less than 100 µm.

11. A process according to claim 9, wherein said gas suspended particles are retained in a suspended state until they have grown to a predetermined weight.

12. A process according to claim 1, wherein the microcrystallized particles are collected from the suspended state on a surface to form a porous agglomerated powder layer.

13. A process according to claim 1, wherein the microcrystallized particles are conditioned at a temperature of about 40-90° C. to a free moisture content below 1%.

14. A process according to claim 1, wherein the microcrystallized particles are conditioned at a temperature of about 67-70° C. to a free moisture content below 1%.

15. A process according to claim 2, wherein the conditioned agglomerated layer is crushed to provide a granular product having a mean granule size of, on an average, 0.05 to 2 mm.

16. A process according to claim 2, wherein the conditioned agglomerated layer is crushed to provide a granular product having a mean granule size of, on an average, 0.1 to 0.4 mm.

* * * * *